(12) United States Patent
Vaughn et al.

(10) Patent No.: US 9,408,789 B2
(45) Date of Patent: Aug. 9, 2016

(54) ANTIPERSPIRANT ACTIVE COMPOSITIONS AND MANUFACTURE THEREOF

(71) Applicant: Colgate-Palmolive Company, Piscataway, NJ (US)

(72) Inventors: John Vaughn, Fair Haven, NJ (US); Iraklis Pappas, Pennsauken, NJ (US); Long Pan, Cherry Hill, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/887,774

(22) Filed: Oct. 20, 2015

(65) Prior Publication Data

US 2016/0106643 A1    Apr. 21, 2016

Related U.S. Application Data

(62) Division of application No. 14/110,721, filed as application No. PCT/US2011/066012 on Dec. 20, 2011, now abandoned.

(60) Provisional application No. 61/479,069, filed on Apr. 26, 2011.

(51) Int. Cl.
*A61K 8/26* (2006.01)
*A61Q 15/00* (2006.01)
(Continued)

(52) U.S. Cl.
CPC ... *A61K 8/26* (2013.01); *A61K 8/19* (2013.01); *A61K 8/20* (2013.01); *A61K 8/28* (2013.01); *A61K 8/44* (2013.01); *A61Q 15/00* (2013.01); *C01F 7/002* (2013.01); *C01F 7/56* (2013.01); *A61K 2800/58* (2013.01); *C01P 2002/86* (2013.01); *C01P 2002/87* (2013.01)

(58) Field of Classification Search
CPC ............ A61K 8/26; A61K 8/19; A61K 8/44; A61K 8/28; A61K 8/20; A61K 2800/58; A61Q 15/00; C01F 7/56; C01F 7/002; C01P 2002/87; C01P 2002/86
See application file for complete search history.

(56) References Cited

U.S. PATENT DOCUMENTS

| 3,979,510 A | 9/1976 | Rubino |
| 3,991,176 A | 11/1976 | Rubino |

(Continued)

FOREIGN PATENT DOCUMENTS

| CA | 2445924 | 5/2004 |
| EP | 0291334 | 11/1988 |

(Continued)

OTHER PUBLICATIONS

Allouche et al., "Conversion of Al13 Keggin ϵ into Al30: a reaction controlled by aluminum monomers", Inorganic Chemistry Communications, 2003, 6:1167-1170.

(Continued)

*Primary Examiner* — Trevor Love

(57) ABSTRACT

An antiperspirant active composition comprising an aluminum salt, the aluminum salt (i) having an aluminum to chloride molar ratio of 0.3:1 to 3:1; and (ii) having a species of polyhydroxyoxoaluminum cation detectable it 76 ppm by $^{27}$Al NMR that is present in a relative abundance on a $^{27}$Al NMR spectrograph that is greater than an other polyhydroxyoxoaluminum cation detectable by $^{27}$Al NMR. Also, disclosed are methods of making the antiperspirant active.

24 Claims, 4 Drawing Sheets

(51) Int. Cl.
*C01F 7/56* (2006.01)
*A61K 8/19* (2006.01)
*A61K 8/44* (2006.01)
*A61K 8/28* (2006.01)
*A61K 8/20* (2006.01)
*C01F 7/00* (2006.01)

(56) References Cited

U.S. PATENT DOCUMENTS

| | | |
|---|---|---|
| 4,871,525 A | 10/1989 | Giovanniello et al. |
| 4,900,534 A | 2/1990 | Inward |
| 5,330,751 A | 7/1994 | Curtin et al. |
| 5,348,720 A | 9/1994 | Vincenti et al. |
| 5,358,694 A | 10/1994 | Giovanniello |
| 5,643,558 A | 7/1997 | Provancal |
| 5,705,171 A | 1/1998 | Iovanni et al. |
| 5,955,065 A | 9/1999 | Thong et al. |
| 5,997,850 A | 12/1999 | Tang et al. |
| 6,010,688 A | 1/2000 | Shen |
| 6,042,816 A | 3/2000 | Shen |
| 6,066,314 A | 5/2000 | Tang et al. |
| 6,074,632 A | 6/2000 | Shen |
| 6,136,302 A | 10/2000 | Juneja et al. |
| 6,149,897 A | 11/2000 | Swaile |
| 6,245,325 B1 | 6/2001 | Shen |
| 6,342,210 B1 | 1/2002 | Cai et al. |
| 6,375,937 B1 | 4/2002 | Chopra et al. |
| 6,428,778 B1 | 8/2002 | Breker et al. |
| 6,436,381 B1 | 8/2002 | Carrillo et al. |
| 6,451,296 B1 | 9/2002 | Li et al. |
| 6,682,749 B1 | 1/2004 | Potechin et al. |
| 6,726,901 B2 | 4/2004 | Yin et al. |
| 6,835,373 B2 | 12/2004 | Kolodzik et al. |
| 6,902,724 B1 | 6/2005 | Parekh et al. |
| 6,936,242 B2 | 8/2005 | Elliott et al. |
| 6,942,850 B2 | 9/2005 | Coe et al. |
| 6,969,510 B2 | 11/2005 | Holerca et al. |
| 7,105,691 B2 | 9/2006 | Holerca et al. |
| 7,189,387 B2 | 3/2007 | Chuah et al. |
| 7,229,611 B2 | 6/2007 | Zamudio-Tena et al. |
| 7,256,875 B2 | 8/2007 | Maier et al. |
| 2004/0101500 A1 | 5/2004 | Ashcroft et al. |
| 2004/0265255 A1 | 12/2004 | Holerca et al. |
| 2005/0265939 A1 | 12/2005 | Li |
| 2006/0153788 A1 | 7/2006 | Swaile et al. |
| 2006/0204463 A1 | 9/2006 | Tang et al. |
| 2006/0292098 A1 | 12/2006 | Scavone et al. |
| 2007/0003499 A1 | 1/2007 | Shen et al. |
| 2007/0020211 A1 | 1/2007 | Li et al. |
| 2007/0110687 A1 | 5/2007 | Mattai et al. |
| 2007/0196302 A1 | 8/2007 | Pratt et al. |
| 2007/0196303 A1 | 8/2007 | Li et al. |
| 2009/0016979 A1 | 1/2009 | Li et al. |

FOREIGN PATENT DOCUMENTS

| | | |
|---|---|---|
| GB | 2144992 | 3/1985 |
| WO | WO 2006/046945 | 5/2006 |
| WO | WO 2006/103092 | 10/2006 |
| WO | WO 2007/004163 | 1/2007 |
| WO | WO 2008/063188 | 5/2008 |
| WO | WO 2008/070218 | 6/2008 |
| WO | WO 2009/075678 | 6/2009 |
| WO | WO 2009/076591 | 6/2009 |
| WO | WO 2012/060817 | 5/2012 |

OTHER PUBLICATIONS

Allouche et al., 2000, "A130: A Giant Aluminum Polycation," Angew Chem. Int. Ed. 39(3):511-514.

Bottero, 1980, "Studies of Hydrolized Aluminum Chloride Solutions, 1. Nature of Aluminum Species and Composition of Aqueous Solutions," The Journal of Physical Chemistry 84:2933-2939.

Casey et al., "Reaction Dynamics, molecular clusters, and aqueous geochemistry," Annu. Rev. Earth Planet. Sci., 2007, 35:21-46.

Casey, "Large aqueous aluminum hydroxide molecules," Chemical Reviews, 2005, 106(1):1-16.

Chen et al, "Effect of thermal treatment on the formation and transformation of Keggin Al13 and Al30 species in hydrolytic polymeric aluminum solutions", Colloids and Surfaces A: Physiochem. Eng. Aspects, 2007, 292:110-118.

Chen et al., 2006, "Evaluation of $Al_{30}$ Polynuclear Species in Polyaluminum Solutions As Coagulant for Water Treatment," Chemosphere 64(6):912-918.

Chen et al., 2009, "On the Acid-Base Stability of Keggin $Al_{13}$ and $Al_{30}$ Polymers in Polyaluminum Coagulants," J. Mater. Sci. 44:3098-3111.

File History from U.S. Appl. No. 12/531,145 through Oct. 20, 2011.

Fu et al., "Aging: processes of alumina sol-gels: characterization of new aluminum polyoxycations by Al NMR Spectroscopy," Chem. Mater., 1991, 3:602-610.

Huang et al., 2006, "Separation and Purification of Nano-$Al_{13}$ by UF Method," Colloids and Surfaces A: Physicochem. Eng. Aspects 275:200-208.

International Search Report and. Written Opinion in International Application No. PCT/US2010/055030, mailed Sep. 1, 2011.

International Search Report in International Application No. PCT/US2007/087145, mailed Apr. 6, 2009.

International Search Report in International Application No. PCT/US2008/086556, mailed Apr. 6, 2009.

International Search Report & Written Opinion for PCT/US2011/066012, mailed May 4, 2012.

Mertens et al., 2012, "Polyahimintun chloride with high Al30 content as removal agent for arsenic-contaminated well water," Water Research 46:53-62.

Muller et al,, "Solid-state aluminum-27 nuclear magnetic resonance chemical shift and quadrupole coupling data for condensed AlO4 tetrahedra," J. Chem. Soc, 1986, pp. 1277-1281.

Rosenberg, "New Antiperspirant Salt Technology," (Cosmetics and Toiletries Manufacture Worldwide, Fondots, D.C. ed., Hartfordshire. UK: Aston Publishing Group) (undated).

Rowsell et al,. "Speciation and thermal transformation in alumina sols: structions of the Polyhydroxyoxoaluminum cluster [Al30O8(OH)56(H20)26]18+ and its δ-Keggin Moieté," J. Am. Chem. Soc., 2000, 122:3777-3778.

Shafran et al, "The static anion exchange method for generation of high purity aluminum polvoxocations and monodisperse aluminum hydroxide nano-panicles", J. Mater. Chem., 2005, 15:3415-3423.

Shafran et al., 2004, "High-Temperature Speciation Studies of Al-Ion Hydrolysis," Advanced Engineering Materials 6(10):836-839.

Shen, 1998, "Synthesis and Speciation of Polyaluminum Chloride for Water Treatment," Environment International 24(8):899-910.

Smart et al., 2013, "Controlled step-wise isomerization of the Keggin-type $Al_{13}$ and determination of the γ-$Al_{13}$ structure," Chemical Communications 49(97):11352-11354.

U.S. Appl. No. 12/531,145, filed Sep. 14, 2009.

Written Opinion in International Application No. PCT/US2010/055030, mailed Nov. 28, 2012.

Zhang et al., 2008, "Coagulation Characteristics of Polyahmiinum Chlorides PAC-Al30 on Humic Acid Removal from Water," Separation & Purification Tech. 63:642-647.

FIGURE 3

ANTIPERSPIRANT ACTIVE COMPOSITIONS AND MANUFACTURE THEREOF

CROSS REFERENCE TO RELATED APPLICATIONS

This application is a divisional application of application Ser. No. 14/110,721, with a 371 entry date of 20 May 2014, which is a 371 application of Application No. PCT/US2011/66012, filed on 20 Dec. 2011, which claims priority to U.S. Provisional Application No. 61/479,069, filed on 26 Apr. 2011, all of which are incorporated herein by reference.

FIELD OF THE INVENTION

The invention relates to antiperspirant active compositions comprising an aluminum salt and to methods of making an antiperspirant active composition.

BACKGROUND OF THE INVENTION

Antiperspirant salts, such as aluminum chlorohydrex (also called aluminum chlorohydrex polymeric salts and abbreviated here as "ACH") and aluminum zirconium glycine salts (abbreviated here as "ZAG", "ZAG complexes" or "AZG"), are known to contain a variety of polymeric and oligomeric species with molecular weights (MW) of 100 Da-500,000 Da. It has been clinically shown that, in general, the smaller the species, the higher the efficacy for reducing sweat.

In an attempt to increase the quality and quantity of smaller aluminum and/or zirconium species, a number of efforts have focused on: (1) how to select the components of ACH and ZAG that affect the performance of these materials; and (2) how to manipulate these components to obtain and/or maintain the presence of smaller types of these components. These attempts have included the development of analytical techniques to identify the components. Size exclusion chromatography ("SEC") or gel permeation chromatography ("GPC") are methods frequently used for obtaining information on polymer distribution in aluminum salt solutions. With appropriate chromatographic columns, generally five distinctive groups of polymer species can be detected in commercial ACH and ZAG complexes appearing in a chromatogram as peaks 1, 2, 3, 4 and a peak known as "5, 6", referred to hereinafter as Peak 5. Peak 1 contains the larger Zr species (greater than 60 Angstroms). Peaks 2 and 3 contain larger aluminum species. Peak 4 contains smaller aluminum species (aluminum oligomers, or small aluminum clusters) and has been correlated with enhanced antiperspirant efficacy for both Al and Al/Zr salts. Peak 5 contains the smallest and most acidic aluminum species. Various analytical approaches for characterizing the peaks of ACH and various types of ZAG actives are found in "Antiperspirant Actives—Enhanced Efficacy Aluminum-Zirconium-Glycine (AZG) Salts" by Dr. Allan H. Rosenberg (Cosmetics and Toiletries Worldwide, Fondots, D. C. ed., Hertfordshire, UK: Aston Publishing Group, 1993, pages 252, 254-256).

Attempts to activate antiperspirant salts to produce materials having improved efficacy have included developing processes for obtaining composition having large amounts of Peak 4, The Applicant's earlier WO-A-2009/076591 discloses, inter alia, an antiperspirant composition having a composition with little or no Peak 3 and optionally little or no Peak 5. However, there is still a need for yet further improved antiperspirant compositions.

Solutions of partially neutralized aluminum are known to contain a variety of hydrolytic Al species. The identity and distribution of these various forms depends on the hydrolysis ratio (i.e. the OH:Al molar ratio), the Al precursor and the choice of the reaction condition. In the field of antiperspirant (AP) technology, SEC chromatography is the traditional method used for elucidating the distribution of these Al species. Conventional SEC physically separates Al species into domains which are subsequently measured using a concentration detector. It is generally recognized that at least five domains of Al species can be differentiated by size-exclusive chromatography. These domains are commonly referred to Peak 1, Peak 2, Peak 3, Peak 4, and Peak 5, where increasing peak number indicates smaller relative size of the eluting species. Peak 4 and Peak 5 have been implicated as highly efficacious Al domains for antiperspirants. Monomeric Al and low oligomers, are known to elute under Peak 5. Oligomeric polyhydroxyoxoaluminum cations elute under Peak 4.

It is well known in the art that such a variety of hydrolytic Al species exists and that it is possible to distinguish large aqueous aluminum hydroxide molecules using spectroscopic methods such as $^{27}Al$ NMR which elucidates the structural environment surrounding Al atoms which are embodied in various forms (Casey W H, "Large Aqueous Aluminum Hydroxide Molecules", Chem. Rev. 2006, 106 (1), pages 1 to 16).

There are two regions in a $^{27}Al$ NMR spectrum that represent Al nuclei which are octahedrally coordinated (0 ppm-60 ppm and tetrahedrally coordinated (60 ppm-90 ppm). The octahedral region is exemplified by the hexa-aqua Al species, i.e. monomeric Al, which resonates sharply at 0 ppm. The tetrahedral region is exemplified by sharp resonance at 62.5 ppm from the $Al_{13}$ polyhydroxyoxoaluminum cation. $Al_{13}$ is composed of 12 octahedrally coordinated Al atoms surrounded by one centrally-cited Al atom which is tetrahedrally coordinated. The $Al_{30}$ polyhydroxyoxoaluminum cation is essentially a dimer of the $Al_{13}$ polyhydroxyoxoaluminum cation and contains 2 tetrahedrally coordinated Al atoms which resonate at 70 ppm.

It is known that $^{27}Al$ NMR spectroscopy may not fully elucidate the chemical composition of a partially neutralized Al salt solution, since there may be a variety of Al species that do not give rise to sharp and unambiguous resonance peaks. These species can be considered as effectively NMR-invisible. Unless the $^{27}Al$ NMR spectroscopy is carried out quantitatively, the relative concentration of these NMR-invisible species cannot be determined and must be inferred from SEC chromatography.

The state of the art discloses a number of methods for synthesizing and purifying the $Al_{13}$ polyhydroxyoxoaluminum cation (for example Fu G, et al, "Aging Processes of Alumina Sol-Gels; Characterization of New Aluminum Polycations by $^{27}Al$ NMR Spectroscopy" Chem. Mater. 1991, 3(4), pages 602 to 610).

It is known that the $Al_{13}$ polyhydroxyoxoaluminum cation may be converted to obtain the $Al_{30}$ polyhydroxyoxoaluminum cation by heating a solution of the $Al_{13}$ polyhydroxyoxoaluminum cation (Roswell J et al, "Speciation and Thermal Transformation in Alumina Sols; Structures of the Polyhydroxyoxoaluminum Cluster $[Al_{30}O_8(OH)_{56}(H_2O)_{26}]^{18+}$ and its δ-Keggin Moieté", J. Am. Chem. Soc. 2000, 122, pages 3777 to 3778; Chen Z et al, "Effect of thermal treatment on the formation and transformation of Keggin $Al_{13}$ and $Al_{30}$ species in hydrolytic polymeric aluminum solutions", Colloids and Surfaces A: Physiochem. Eng. Aspects, 292 (2007) pages 110 to 118; and Allouche L et al, "Conversion of $Al_{13}$ Keggin ε into $Al_{30}$: a reaction controlled by aluminum monomers", Inorganic Chemistry Communications, 6 (2003) pages 1167-1170).

Heating, an $Al_{13}$ solution is the only synthetic pathway to achieving $Al_{30}$ which has been described in the literature. As well as the references identified above, WO-A-2006/103092 and Shafran K L et al, "The static anion exchange method for generation of high purity aluminum polyoxocations and monodisperse aluminum hydroxide nano-particles", J. Mater. Chem., 2005, 15, pages 3415 to 3423, disclose the use of an ion-exchange process to synthesize $Al_{13}$ to achieve greater than 90% purity, and disclose heating the thus-formed $Al_{13}$ solution to form $Al_{30}$.

Partial neutralization of Al salts have been shown to yield trace quantities of the polyhydroxyoxoaluminum cation detectable at 76 ppm by $^{27}Al$ NMR. There is a need in the art for a high-yield synthetic route to the polyhydroxyoxoaluminum cation detectable at 76 ppm by $^{27}Al$ NMR. The small quantities obtained, lack of purity, and lack of method of making has prevented science from isolating this polycation in sufficient quantity and purity so that its structure could be determined.

There is a need in the art for aluminum antiperspirant actives which have high antiperspirant efficacy.

There is also a need in the art for aluminum antiperspirant actives which have high stability.

There is also a need in the art for aluminum antiperspirant actives which have the combination of high antiperspirant efficacy and high stability.

BRIEF DESCRIPTION OF THE DRAWINGS

FIG. 3 is a $^{27}Al$ NMR spectrograph of material 2 from the examples before heating.

BRIEF SUMMARY OF THE INVENTION

Figure 1:
FIG. 1 is a $^{27}Al$ NMR spectrograph of material 1 from the examples before heating.

The present invention is based on modifying the composition from the inventors' earlier work, which was filed as PCT/US2010/55030 on 2 Nov. 2011. It has been discovered that the $Al_{30}$ in antiperspirant salt can be converted to a species of polyhydroxyoxoaluminum cation detectable at 76 ppm by $^{27}Al$ NMR. This species also will elute at Peak 4 on as SEC chromatogram.

The previous material can be aged for a sufficient time at sufficient temperature to convert the $Al_{30}$. In one embodiment, the material can be aged at about 100° C. for a sufficient period of time, such as about 10 days or greater, or about 30 days or greater. In another embodiment, the material can aged by supercritical heating in an isochoric reaction vessel or under hydrothermal reaction at sufficient temperature and time, such as at 100° C. for 5 days. In another embodiment, the material can be aged at ambient conditions (such as 15° C. to 60° C.) for a period of time of several months, such as at least 6 months, to more than one year.

The present invention accordingly provides antiperspirant active composition comprising an aluminum salt, the aluminum salt (i) having an aluminum to chloride molar ratio of 0.3:1 to 3:1; and (ii) having a species of polyhydroxyoxoaluminum cation detectable at 76 ppm by $^{27}Al$ NMR that is present in a relative abundance on a $^{27}Al$ NMR spectrograph that is greater than any other polyhydroxyoxoaluminum cation detectable by $^{27}Al$ NMR.

In other embodiments, the species of polyhydroxyoxoaluminum cation detectable at 76 ppm by $^{27}Al$ NMR is present in an amount that is a majority of a total amount of all species of polyhydroxyoxoaluminum cations detectable by $^{27}Al$ NMR. In other embodiments, the species of polyhydroxyoxoaluminum cation detectable at 76 ppm by $^{27}Al$ NMR is present in an amount that is at least 50, 55, 60, 65, 70, 75, 80, 85, 90, 95, 96, 97, 98, 99, 99.5, 99.9, 99.99, or 99.999% of a total amount of all species of polyhydroxyoxoaluminum cations detectable by $^{27}Al$ NMR.

Optionally, the aluminum salt exhibits a SEC chromatogram having a SEC Peak 4 area of at least 90% of a total area of Peaks 1, 2, 3, 4 and 5 in the SEC chromatogram.

In this specification, the SEC chromatogram is measured using an aqueous solution of the aluminum salt.

In some embodiments, the $^{27}Al$ NMR spectrum has a species distribution including at most 5% $Al_{13}$ polyhydroxyoxoaluminum cation in the species detectable by $^{27}Al$ NMR within the aluminum salt. In some embodiments, the $^{27}Al$ NMR spectrum has a species distribution including no $Al_{13}$ polyhydroxyoxoaluminum cation in the species detectable by $^{27}Al$ NMR within the aluminum salt. In some embodiments, the $^{27}Al$ NMR spectrum has a species distribution including at most 5% $Al_m$. $Al_m$ comprising an aluminum-and chloride-containing monomer, in the species detectable by $^{27}Al$ NMR within the aluminum salt.

In some embodiments, the aluminum salt has an OH to Al ratio of at most 2.6:1, and in other embodiments 2:1 to 2.6:1, optionally an OH to Al ratio of 2:1 to 2.5:1, or 2.3:1 to 2.5:1.

The antiperspirant active composition may optionally further comprise a buffer, wherein a molar ratio of buffer to aluminum is at least 0.1:1. In other embodiments, the molar ratio is 0.1:1 to 3:1. The buffer may be at least one buffer chosen from an amino acid, betaine, and quat. Optionally, the buffer is an amino acid and a molar ratio of amino acid to aluminum is at least 0.1:1. In some embodiments, the amino acid is glycine.

In some embodiments, the composition has a SEC Peak 4 area of at least 95% of a total area of Peaks 1, 2, 3, 4 and 5 in the SEC chromatogram. In some embodiments, the composition has a SEC Peak 3 area of less than 5% of a total area of Peaks 1, 2, 3, 4 and 5 in the SEC chromatogram, and most preferably has no SEC Peak 3 area in the SEC chromatogram.

In some embodiments, the composition has a SEC Peak 5 area of less than 5% of a total area of Peaks 1, 2, 3, 4 and 5 in the SEC chromatogram, and most preferably has no SEC Peak 5 area in the SEC chromatogram.

In some embodiments, the antiperspirant active composition has a SEC Peak 4 area of 95 to 100%, no SEC Peak 3 area, and a SEC Peak 5 area of from 0 to 5% of a total area of Peaks 1, 2, 3, 4 and 5 in the SEC chromatogram.

The antiperspirant active composition may further comprise zirconium, and optionally a molar ratio of aluminum to zirconium is 5:1 to 10:1.

A method of making an antiperspirant active composition comprising:
I) heating an aqueous solution containing i) a first aluminum salt containing an $Al_{30}$ polyhydroxyoxoaluminum cation and having an aluminum to chloride molar ratio of 0.3:1 to 3:1, ii) an inorganic salt, and iii) a buffer, wherein the buffer is at least one of an amino acid, betaine, and quat and a molar ratio of buffer to aluminum is at least 0.1:1, wherein the heating is one of a) at a temperature of 100° C. to 250° C. in an isochoric reactor or under hydrothermal reaction for a time sufficient to form a species of polyhydroxyoxoaluminum cation detectable at 76 ppm by $^{27}$Al NMR; or b) at 100° C. at reflux for about 10 days or greater, optionally about 30 days or greater to form a fourth aluminum salt.

The present invention also provides a method of making an antiperspirant active composition comprising:

I) heating an aqueous solution containing a first aluminum salt having an aluminum to chloride molar ratio of 0.3:1 to 3:1 and a buffer, wherein the buffer is at least one of an amino acid, betaine, and quat and a molar ratio of buffer to aluminum is at least 0.1:1, at a temperature of 50° C. to 100° C. for a period of time of 1 hour to 6 hours to obtain a first aluminum salt solution;

II) adding to the first aluminum salt solution an aqueous solution of an inorganic base to obtain a second pH adjusted aluminum salt solution having an OH:Al molar ratio of at most 2.6:1, or optionally 2:1 to 2.6:1, and a pH of 2 to 5;

III) heating the second pH adjusted aluminum salt solution at a temperature of 50° C. to 100° C. for a period of time of at least 6 hours to obtain a third aluminum salt solution containing an $Al_{30}$ polyhydroxyoxoaluminum cation;

IV) heating the third aluminum salt solution at one of
a) at a temperature of 100° C. to 250° C. in an isochoric reactor or under hydrothermal reaction for a time sufficient to form a species of polyhydroxyoxoaluminum cation detectable at 76 ppm by $^{27}$Al NMR; or
b) at 100° C. at reflux for about 10 days or greater, optionally about 30 days or greater;
to form a fourth aluminum salt; and V) optionally adding an aqueous solution containing a zirconium compound to the second pH adjusted aluminum salt solution to thereby obtain a second pH adjusted aluminum-zirconium salt solution having a molar ratio of aluminum to zirconium of 5:1 to 10:1.

The present invention also provides a method of making a polyhydroxyoxoaluminum cation detectable at 76 ppm by $^{27}$Al NMR comprising storing an aqueous solution containing i) the aluminum salt containing an $Al_{30}$ polyhydroxyoxoaluminum cation and having an aluminum to chloride molar ratio of 03:1 to 3:1, ii) an inorganic salt, and iii) a buffer, wherein the buffer is at least one of an amino acid, betaine, and quat, and a molar ratio of buffer to aluminum is at least 0.1:1 at a temperature of 15° C. to 60° C. for a period of time until the polyhydroxyoxoaluminum cation detectable at 76 ppm by $^{27}$Al NMR that is present in a relative abundance on a $^{27}$Al NMR spectrograph that is greater than any other polyhydroxyoxoaluminum cation detectable by $^{27}$Al NMR.

In some embodiments, the buffer is glycine. In some embodiments, the inorganic salt is at least one chloride salt chosen from calcium chloride, magnesium chloride, strontium chloride, barium chloride, stannous chloride, and yttrium chloride. In some embodiments, the inorganic base includes at least one member chosen from calcium hydroxide, magnesium hydroxide, strontium hydroxide, barium hydroxide, stannous hydroxide, yttrium hydroxide, calcium oxide, magnesium oxide, strontium oxide, barium oxide, stannous oxide, yttrium oxide, calcium carbonate, magnesium carbonate, strontium carbonate, barium carbonate, stannous carbonate, and yttrium carbonate. Typically, the inorganic base is calcium hydroxide. In some embodiments, the aluminum salt solution has an OH to Al molar ratio of 2.0:1 to 2.5:1 or 2.1:1 to 2.5:1.

In some embodiments, the first aluminum salt is an aluminum chloride compound chosen from aluminum trichloride, aluminum chlorohexahydrate, aluminum dichlorohydrate, and aluminum monochlorohydrate. Optionally, the composition further comprises zirconium. The zirconium compound may be $ZrOCl_2 \cdot 8H_2O$ or Oxo-Hexameric Zirconium-Octaamino Acid.

In some embodiments, the fourth aluminum salt has a SEC Peak 4 area of at least 95% of a total area of Peaks 1, 2, 3, 4 and 5 in the SEC chromatogram. In some embodiments, the fourth aluminum salt has a SEC Peak 3 area of less than 5% of a total area of Peaks 1, 2, 3, 4 and 5 in the SEC chromatogram, and preferably the fourth aluminum salt has no SEC Peak 3 area in the SEC chromatogram. In some embodiments, the fourth aluminum salt has a SEC Peak 5 area of less than 5% of a total area of Peaks 1, 2, 3, 4 and 5 in the SEC chromatogram.

In some embodiments, in step III) the period of time is at least 12 hours, or in some embodiments at least 24 hours.

The present invention further provides the use of a heating step to convert $Al_{30}$ polyhydroxyoxoaluminum cations in the species detectable by $^{27}$Al NMR within an aqueous aluminum salt solution into a species of polyhydroxyoxoaluminum cation detectable at 76 ppm by $^{27}$Al NMR, the aqueous aluminum salt solution i) having an aluminum to chloride molar ratio of 0.3:1 to 3:1; ii) an inorganic salt, and iii) a buffer, wherein the buffer is at least one of an amino acid, betaine, and quat, and a molar ratio of buffer to aluminum is at least 0.1:1; an OH:Al molar ratio of at most 2.6:1, or optionally, 2:1 to 2.6:1; and the heating step is one of:

a) at a temperature of 100° C. to 250° C. in an isochoric reactor or under hydrothermal reaction for a time sufficient to form a species of polyhydroxyoxoaluminum cation detectable at 76 ppm by $^{27}$Al NMR; or b) at 100° C. at reflux for about 10 days or greater, optionally about 30 days or greater.

In some embodiments, the heating step converts all the $Al_{13}$ polyhydroxyoxoaluminum cation species present in the aqueous aluminum salt solution into the $Al_{30}$ polyhydroxyoxoaluminum cation species. In some embodiments, the heating step reduces a SEC Peak 5 area in the SEC chromatogram. Optionally, the period of time is at least 12 hours or, in other embodiments, at least 24 hours. In some embodiments, the buffer is glycine.

In some embodiments, the OH:Al molar ratio has been achieved by adding to the aqueous aluminum salt solution an inorganic base including at least one member chosen from calcium hydroxide, magnesium hydroxide, strontium hydroxide, barium hydroxide, stannous hydroxide, yttrium hydroxide, calcium oxide, magnesium oxide, strontium oxide, barium oxide, stannous oxide, yttrium oxide, calcium carbonate, magnesium carbonate, strontium carbonate, barium carbonate, stannous carbonate, and yttrium carbonate. Typically, the inorganic base is calcium hydroxide. Optionally, the OH to Al molar ratio is 2.0:1 to 2.5:1 or 2.1:1 to 2.5:1.

In some embodiments, the aluminum salt is an aluminum chloride compound chosen from aluminum trichloride, acidified aluminum chlorohexahydrate, aluminum dichlorohydrate, and aluminum monochlorohydrate.

In some embodiments, the heating increases the $Al_{30}$ polyhydroxyoxoaluminum cation species in the $^{27}$Al NMR spectrum from at least 90% to at least 95% of the species detectable by $^{27}$Al NMR within the aluminum salt.

In some embodiments, after the heating step the aluminum salt has a SEC Peak 4 area of at least 95% of a total area of Peaks 1, 2, 3, 4 and 5 in the SEC chromatogram. In some embodiments, after the heating step the aluminum salt has a SEC Peak 3 area of less than 5% of a total area of Peaks 1, 2, 3, 4 and 5 in the SEC chromatogram, and preferably has no SEC Peak 3 area in the SEC chromatogram. In some embodiments, after the heating step the aluminum salt has a SEC Peak 5 area of less than 5% of a total area of Peaks 1, 2, 3, 4 and 5 in the SEC chromatogram.

The present invention further provides an antiperspirant active composition including an aluminum salt produced by the method of the invention or the use of the invention.

DETAILED DESCRIPTION OF THE INVENTION

In this specification, the use of $^{27}$Al NMR data is not quantitative but considers only NMR-visible Al species and in particular resonances at 0 ppm, 62.5 ppm, 70 ppm, and 76 ppm. Octahedrally coordinated nuclei are detected via $^{27}$Al NMR. The Al monomer resonance at 0 ppm is octahedrally coordinated. Octahedral bands in $Al_{13}$ and $Al_{30}$ are broad and overlapping, so they're not useful when identifying Al species. The breadth of octahedral bands in $Al_{13}$ & $Al_{30}$ is due to structural and environmental variation. Because the Al nuclei in monomeric Al exist structurally in one form, the signal is narrow, and easily identified. Tetrahedrally coordinated nuclei in $Al_{13}$ and $Al_{30}$ also feature minimal variation, which leads to narrow, identifiable NMR signals. $^{27}$Al NMR data do not indicate the amount of undetected Al embodied in NMR-invisible species.

When calculating, the relative amounts of Al embodied in compositions contain $^{27}$Al NMR visible species that have known structures, such as $Al_{13}$ and $Al_{30}$ polyhydroxyoxoaluminum cations, the tetrahedral resonance peak of the aluminum is integrated and multiplied by a scaling factor to account for other octahedrally coordinated Al present in the structure. In the $Al_{13}$ polyhydroxyoxoaluminum cation, there is one tetrahedral resonance peak in the structure. In the $Al_{30}$ polyhydroxyoxoaluminum cation, there are two tetrahedral resonance peaks in the structure. To convert, the resonance from the $Al_{13}$ polyhydroxyoxoaluminum cation is multiplied by 13, whereas the resonance from the $Al_{30}$ polyhydroxyoxoaluminum cation is multiplied by 15. When the structure of the 76 ppm material is identified, a scaling factor can be determined.

For now, the amounts of each species of polyhydroxyoxoaluminum cation in a composition will be characterized by the relative abundance of tetrahedral aluminum resonance peaks on a $^{27}$Al NMR spectrograph. This means that the area of the tetrahedral aluminum resonance peak for a polyhydroxyoxoaluminum cation is compared to the area of the tetrahedral aluminum resonance peaks for other polyhydroxyoxoaluminum cations. The $^{27}$Al NMR spectrograph should be collected at sufficient enough field strength so that all relevant signals can be integrated. One procedure for operating a $^{27}$Al NMR is described in the examples below. In the current state of the art, the resonance frequency is at least 104.2 Mhz to provide a sufficient field strength.

The present invention is directed to antiperspirant active composition comprising an aluminum salt, the aluminum salt (i) having an aluminum to chloride molar ratio of 0.3:1 to 3:1; and (ii) having a species of polyhydroxyoxoaluminum cation detectable at 76 ppm by $^{27}$Al NMR that is present in a relative abundance on a $^{27}$Al NMR spectrograph that is greater than any other polyhydroxyoxoaluminum cation detectable by $^{27}$Al NMR.

In certain embodiments, the species of polyhydroxyoxoaluminum cation detectable at 76 ppm by $^{27}$Al NMR is present in an amount that is at least 50, 55, 60, 65, 70, 75, 80, 85, 90, 95, 96, 97, 98, 99, 99.5, 99.9, 99.99, or 99.999% of a total amount of all species of polyhydroxyoxoaluminum cation detectable by $^{27}$Al NMR. In other embodiments, the species of polyhydroxyoxoaluminum cation detectable at 76 ppm by $^{27}$Al NMR is present in an amount that is a majority of a total amount of all species of polyhydroxyoxoaluminum cations detectable by $^{27}$Al NMR.

The species of polyhydroxyoxoaluminum cation detectable at 76 ppm by $^{27}$Al NMR can be made by heating an aqueous solution containing a lust aluminum salt containing an $Al_{30}$ polyhydroxyoxoaluminum cation and having an aluminum to chloride molar ratio of 03:1 to 3:1, ii) an inorganic salt, and iii) a buffer, wherein the buffer is at least one of an amino acid, betaine, and quat, and a molar ratio of buffer to aluminum is at least 0.1:1, wherein the heating is one of a) at a temperature of 100° C. to 250° C. in an isochoric reactor or under hydrothermal reaction for a time sufficient to form a species of polyhydroxyoxoaluminum cation detectable at 76 ppm by $^{27}$Al NMR; or b) at 100° C. at reflux for about 10 days or greater, optionally about 30 days or greater.

The reaction in the isochoric reactor is conducted at 100° C. to 250° C. As the temperature increases, the time need to convert $Al_{30}$ polyhydroxyoxoaluminum cation to the polyhydroxyoxoaluminum cation detectable at 76 ppm by $^{27}$Al NMR decreases. Below are some examples of temperature and time:

i) at 100° C. for about 5 days,
ii) at 120° C. for about 12 hours, or
iii) at 150° C. for about 20 minutes.

The inorganic salt and buffer help to stabilize the species of polyhydroxyoxoaluminum cation detectable at 76 ppm by $^{27}$Al NMR. In certain embodiments, the inorganic salt is at least one chloride salt chosen from calcium chloride, strontium chloride, barium chloride, magnesium chloride, stannous chloride, and yttrium chloride. In one embodiment, the salt is calcium chloride. In certain embodiments, the buffer is glycine. In certain embodiments, the inorganic salt is calcium chloride and the buffer is glycine.

The present invention can provide an antiperspirant active composition having a high SEC peak 4 in aqueous solution. The composition is obtained by a stepwise procedure to neutralize aluminum chloride in a solution (optionally buffered) using inorganic bases. In some embodiments, the antiperspirant active compositions obtained by this stepwise procedure include aluminum salts having an aluminum to chloride molar ratio of 0.3:1 to 3:1, optionally, the aluminum salt exhibits a SEC chromatogram having a SEC Peak 4 area of at least 90% of a total area of Peaks 1, 2, 3, 4 and 5 in the SEC chromatogram in aqueous solution. The composition may optionally include zirconium.

The description below describes methods of obtaining an $Al_{30}$ polyhydroxyoxoaluminum cation containing composition.

The $Al_{30}$ containing compositions may be made in a variety of ways involving a stepwise procedure to neutralize aluminum chloride in solution (optionally buffered) using inorganic basic salts. The procedure generally includes the step of heating an aqueous solution containing an aluminum chloride compound (optionally with a buffer agent) at a temperature of 50° C. to 100° C., optionally 50° C. to 95° C., for a period of time of 1 hour to 6 hours. The heating may be under stirring, such as vigorous stirring, or under reflux. In one such embodiment, an aqueous solution containing an aluminum chloride compound and a buffer agent is heated at a temperature of 75° C. to 95° C. to reflux for a period of time of 2 hours to 4 hours. In one embodiment, the temperature is 95° C. under vigorous stirring for a period of time of 2.5 hours.

To adjust the pH of the aluminum salt solution, an aqueous solution of an inorganic base is added to the heated solution to thereby obtain a pH adjusted aluminum salt solution having a hydroxide to aluminum molar ratio of 1:1 to 4:1, and a pH of 2 to 5. In one such embodiment, the hydroxide to aluminum molar ratio of 2:1 to 3:1. In another such embodiment, the hydroxide to aluminum molar ratio is 2.1:1 to 2.6:1.

In one embodiment, the inorganic base can be at least one base chosen from metal hydroxides, calcium hydroxide, magnesium hydroxide, strontium hydroxide, barium hydroxide, stannous hydroxide, yttrium hydroxide, calcium oxide, magnesium oxide, strontium oxide, barium oxide, stannous oxide, yttrium oxide, calcium carbonate, magnesium carbonate, strontium carbonate, barium carbonate, stannous carbonate, and yttrium carbonate.

Optionally, a buffer can be included. Buffers that can be used can be chosen from amino acids, such as glycine, and betaine, such as betaine monohydrate, or quats. The buffer to aluminum molar ratio in certain embodiments can be at least 0.1:1, or 0.1:1 to 3:1. In another embodiment, the buffer to aluminum molar ratio is 0.1:1 to 2:1.

In one embodiment, the inorganic base is calcium hydroxide. In one such embodiment, the addition of calcium hydroxide provides an aqueous solution having a Ca(OH)$_2$:glycine molar ratio of at least 0.1:1.

When a buffer is absent, significant Peak 3 species in the SEC chromatogram begin to form when the total Al concentration is above 0.2M. When a buffer is present, the total Al concentration can reach up to 2.5M while maintaining a predominant Peak 4 in the SEC chromatogram. In one embodiment, an aqueous aluminum chloride salt solution is buffered with glycine and held at 50° C. to 95° C. under vigorous stirring for a period time of 1 to 6 hours. To the heated solution, an aqueous solution of an inorganic base is added dropwise over a period of time of 1 to 3 hours while maintaining the aluminum-glycine solution at 50° C. to 95° C. under vigorous stirring. In one such embodiment, the solution has a glycine to aluminum molar ratio of 1.5. In another such embodiment, the solution has a glycine to aluminum molar ratio of 0.5.

In some embodiments, a zirconium salt may also be added to the pH adjusted aluminum salt solution. In one other such embodiment, the molar ratio of Al:Zr is 5:1 to 10:1. The zirconium salt may be simple Zr salts: ZrOCl$_2$.8H$_2$O or Oxo-Hexameric Zirconium-Octaamino Acid. In one such embodiment, the molar ratio of Al:Zr is 8. In another such embodiment, the molar ratio of Al:Zr is 7. In one other such embodiment, the molar ratio of Al:Zr is 9.

For the above methods, the aluminum chloride salt and inorganic base may be obtained from a variety of sources. In one embodiment, the aluminum chloride salt includes aluminum trichloride, acidified aluminum chlorohexahydrate, aluminum dichlorohydrate, and aluminum monochlorohydrate. In one such embodiment, the aluminum chloride salt is aluminum chlorohexahydrate.

The present invention provides for aluminum antiperspirant active compositions and/or aluminum-zirconium antiperspirant active compositions having high levels of low molecular weight Al and Zr species. The high levels of low molecular weight Al and Zr species is reflected in a SEC trace that has an intense Peak 4 and low Peaks 1, 2, 3 and 5. The polymerization of the antiperspirant actives in aqueous solutions and the correspondent gelation process were followed by monitoring the molecular weight profile of the polyoxohalides in time by SEC. The relative retention time ("Kd") for each of these peaks varies depending on the experimental conditions, but the peaks remain relative to each other. The SEC data for the examples was obtained using an SEC chromatogram using the following parameters: Waters®600 analytical pump and controller, Rheodyne® 77251 injector, Protein-Pak® 125 (Waters) column, Waters 2414 Refractive Index Detector. 5.56 mM nitric acid mobile phase, 0.50 ml/min flow rate, 2.0 microliter injection volume. Data was analyzed using Waters® Empower software (Waters Corporation, Milford, Mass.). The concentration of the antiperspirant in aqueous solution does not affect the retention time in the machine.

The design of modern antiperspirant (AP) salts aims at actives with high levels of low molecular weight Al and Zr species, which is reflected in a SEC trace that has intense Peak 4 and low Peaks 1, 2, and 3, and optionally low Peak 5. Throughout the present study, the levels of the species corresponding to these peaks are estimated based on the following ratios (or percentages):

$$f_{Pi} = \frac{Pi}{\sum Pj} i = 1, 2, 3, 4, 5;$$

$$j = 2, 3, 4, 5$$

where $f_{Pi}$ is the fraction of peak i, and Pi or Pj are the intensity of peaks Pi or Pj, respectively. The amount of low molecular weight Al species will be correlated with the fraction, $f_{P4}$, or percentage, $f_{P4} \times 100$, of SEC-Peak 4. In brief, a preferred antiperspirant salt would have a very low $f_{P1}$, $f_{P2}$, $f_{P3}$, and/or $f_{P5}$, and a high $f_{P4}$.

In certain embodiments, the ratio of Peak 4 to Peak 3 is at least 8, 9, 10, 11, 12, 13, 14, 15, 16, 17, 18, 19, 20, 25, 30, 35, 40, 45, 50, 60, 70, 80, 90, 100, or any number up to infinity. Preferably, Peak 3 is so low as to be undetectable.

In one embodiment, an aluminum salt and/or aluminum-zirconium salt, in aqueous solution, exhibit a SEC profile wherein the SEC Peak 4 to Peak 3 intensity ratio is even as high as infinity, because the Peak 3 is undetectable. In some embodiments, the percentage of SEC Peak 4 of a total area of Peaks 1, 2, 3, 4 and 5 in the SEC chromatogram is: at least at least 90%; at least 95%, or 95 to 100%. In another such embodiment, the SEC Peak 4 area is 100%.

In another embodiment, the aluminum salt and/or the aluminum-zirconium salt, in aqueous solution, exhibits a SEC profile which exhibits low percentage of SEC Peak 3. In such embodiments, the composition has the percentage of SEC Peak 3 area of a total area of Peaks 1, 2, 3, 4 and 5 in the SEC chromatogram is: less than 5%; less than 2%; less than 1%; less than 0.9%: less than 0.8%; less than 0.7%; less than 0.6%; of less than 0.5%; less than 0.4%; less than 0.3%; less than 0.2%; or less than 0.1%. In another such embodiment, the composition has no SEC Peak 3 area.

In another embodiment, the aluminum salt and/or the aluminum-zirconium salt, in aqueous solution, exhibits a SEC profile which exhibits low percentages of SEC Peak 5. In such embodiments, the percentage of SEC Peak 5 area of a total area of Peaks 1, 2, 3, 4 and 5 in the SEC chromatogram is: less than 5%; or less than 1%. In another such embodiment, the composition has no SEC Peak 5 area.

In other embodiments, the aluminum salt and/or the aluminum-zirconium salt, in aqueous solution, exhibits a SEC profile which exhibits a low percentage of SEC Peak 1 and a low percentage of SEC Peak 2. In such embodiments, the percentage of SEC Peak 1 area of a total area of Peaks 1, 2, 3, 4 and 5 in the SEC chromatogram is less than 5%; less than 2%; or less than 1%, or the salt has no SEC Peak 1 area. In other embodiments, the percentage of SEC Peak 2 area of a total area of Peaks 1, 2, 3, 4 and 5 in the SEC chromatogram is less than 5%; less than 2% or less than 1%; or the salt has no SEC Peak 2 area. Preferably, the salt has no Peak 1 area and no Peak 2 area. More preferably, the salt has no Peak 1 area, no Peak 2 area and no Peak 3 area. Yet more preferably, the salt has no Peak 1 area, no Peak 2 area, no Peak 3 area and no Peak 5 area.

The aluminum antiperspirant active compositions and/or aluminum-zirconium antiperspirant active compositions may be used in a variety of antiperspirant products. If the product is used as a solid powder, the size of the particles of antiperspirant active of the invention can be any desired size, and may include conventional sizes such as in the range of 2 to 100 microns, with selected grades having an average particle size of 30-40 microns; finer sized grades having an average particle size distribution of 2-10 microns with an average size of 7 microns as made by a suitable dry-grinding method; and micronized grades having an average particle size of less than or equal to 2 microns, or less than or equal to 1.5 microns.

The compositions of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions. These antiperspirant actives can be used as the antiperspirant active in any antiperspirant composition. Examples of formulations can be found in WO20091076591.

The present invention is exemplified by the following non-limiting Examples.

EXAMPLES

Two materials prepared in accordance with PCT/US2010/55030 are provided. The materials are aqueous systems that contain the glycine buffer and the calcium chloride byproduct of the manufacturing process.

Figure 2:
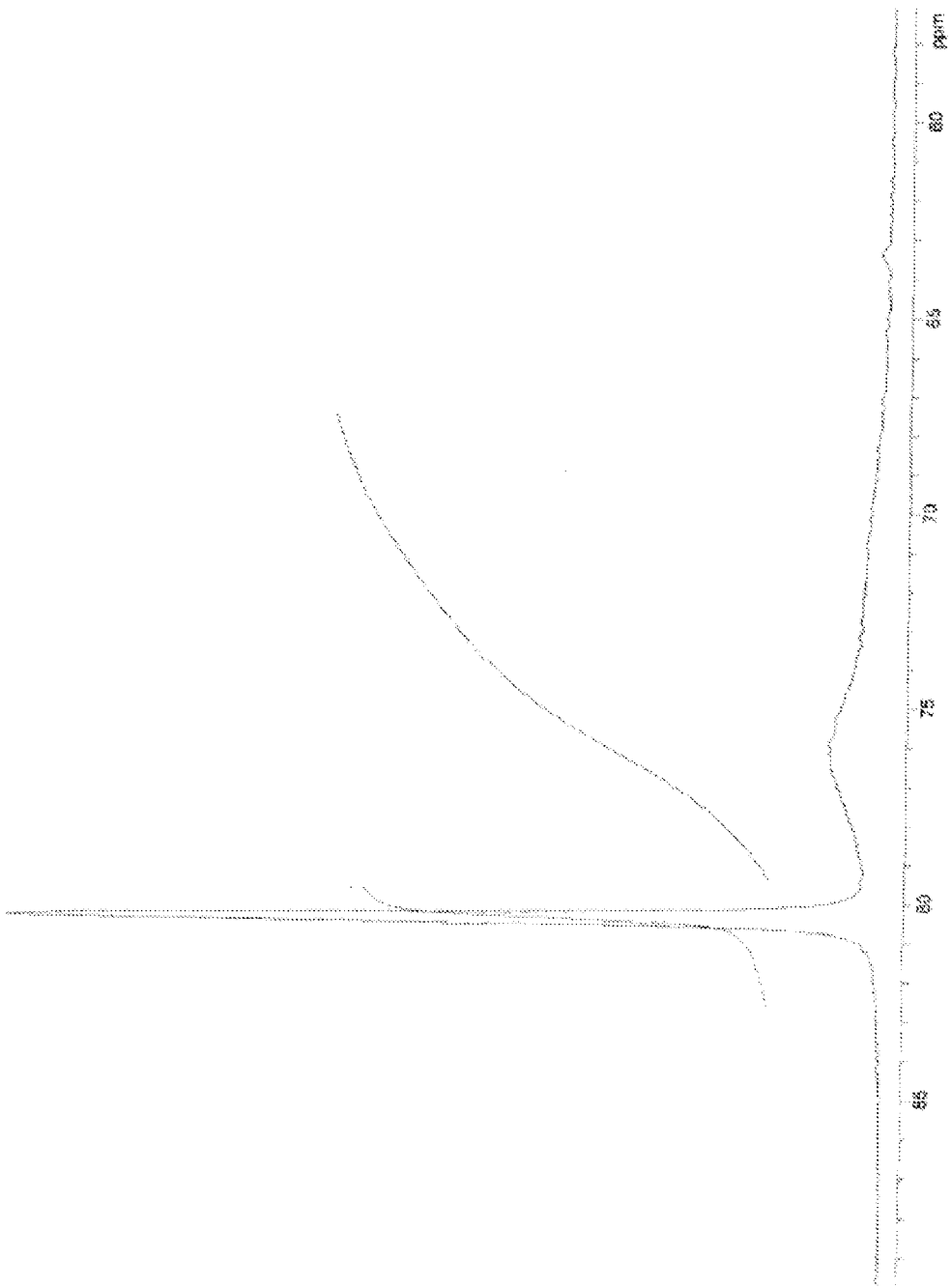
FIG. 2 is a $^{27}Al$ NMR spectrograph of material 1 from the examples after heating.
Figure 3:
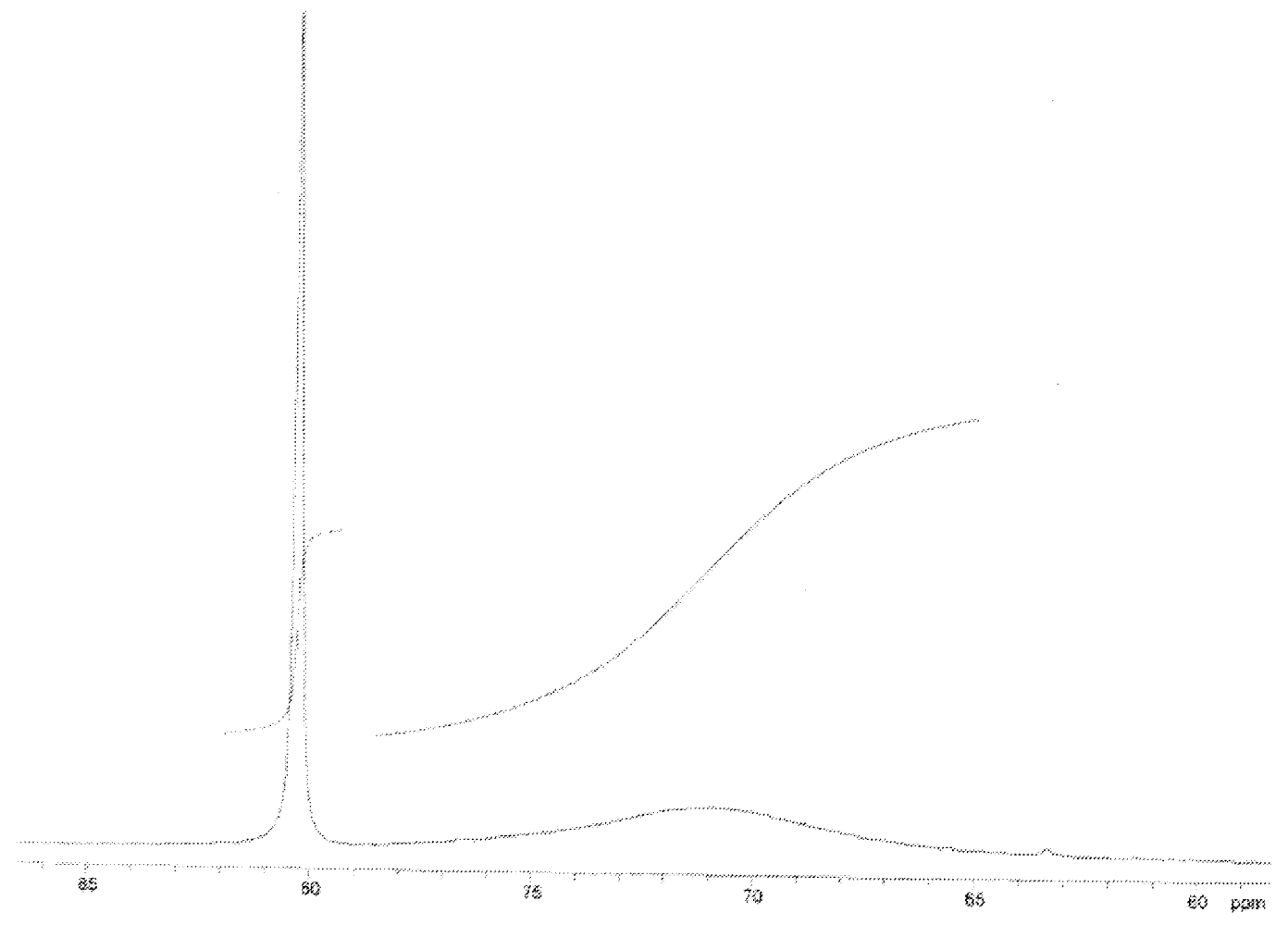
Figure 4:
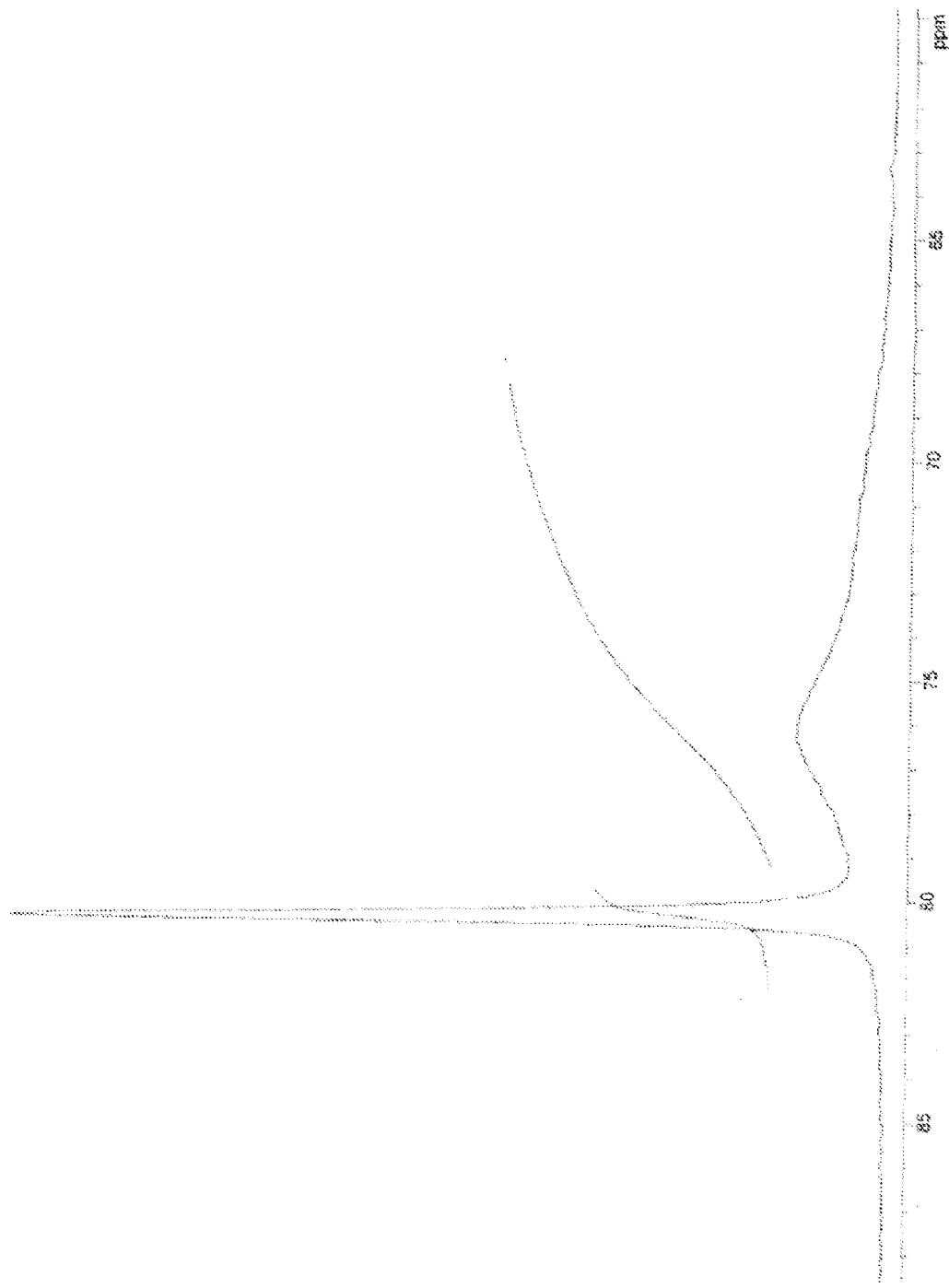
FIG. 4 is a $^{27}Al$ NMR spectrograph of material 2 from the examples after heating.

The raw integration values for $^{27}$Al NMR spectroscopy peaks for these materials are listed below in Table 1, and Table 2 shows the relative abundance. The materials are analyzed by taking a 1 M solution and diluting in a 1:4 ratio using $D_2O$. The final Al concentration for all samples is 0.25M. The samples are analyzed at a $^{27}$Al resonance frequency of 104.2 MHz at 90° C. A coaxial insert containing $NaAlO_2$ is included to provide a reference resonance peak at 80 ppm. The instrument collects 1500 transients, with a pulse width of 6.4 μs and a delay time of 2 seconds. The data for the relevant peaks are shown in the tables below. The full spectrographs can be seen in FIGS. 1 to 4.

Materials 1 is held at reflux for 30 days at 100° C. Material 2 is subjected to 100° C. for 5 days in an isochoric reaction vessel. For comparative purposes, the following discussion relates only with the relative integrations instead of raw data.

For Material 1, the $Al_{30}$ signal (encompassing 96.10% of the total visible tetrahedral Al) is converted to a signal at 76 ppm (97.76% Td Al). Also, the amount of $Al_{13}$ is reduced from 1.90% to 2.24%.

For Material 2, the $Al_{30}$ signal at 70 ppm (encompassing 98.44% of the total visible tetrahedral Al) is converted to a signal at 76 ppm (99.37% Td Al). Also, the amount of $Al_{13}$ is reduced from 1.56% to 0.63%.

TABLE 1

| Material | 76 ppm | 70 ppm | 63 ppm | Total Visible $T_d$ Al |
|---|---|---|---|---|
| Material 1 untreated | None detected | 906.11 | 36.75 | 942.86 |
| Material 1 treated | 1054.37 | None detected | 24.15 | 1078.52 |
| Material 2 untreated | None detected | 1581.97 | 25.09 | 1611.06 |
| Material 2 Treated | 1453.69 | None detected | 9.20 | 1462.89 |

TABLE 2

| | Relative Abundance % | | |
|---|---|---|---|
| Material | 76 ppm | 70 ppm | 63 ppm |
| Material 1 untreated | 0 | 96.10 | 3.90 |
| Material 1 treated | 97.76 | 0 | 2.24 |
| Material 2 untreated | 0 | 98.44 | 1.56 |
| Material 2 Treated | 99.37 | 0 | 0.63 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A method of making an antiperspirant active composition comprising:
   I) heating an aqueous solution containing i) a first aluminum salt containing an $Al_{30}$ polyhydroxyoxoaluminum cation and having an aluminum to chloride molar ratio of 0.3:1 to 3:1, ii) an inorganic salt, and iii) a buffer, wherein the buffer is at least one of an amino acid, betaine, and quat, and a molar ratio of buffer to aluminum is at least 0.1:1, wherein the heating forms a fourth aluminum salt and is one of
      a) at a temperature of 100° C. to 250° C. in an isochoric reactor or under hydrothermal reaction for a time sufficient to form a species of polyhydroxyoxoaluminum cation detectable at 76 ppm by, $^{27}$Al NMR; or
      b) at 100° C. at reflux for about 10 days or greater.

2. A method of making an antiperspirant active composition comprising:
   I) heating an aqueous solution containing a first aluminum salt having an aluminum to chloride molar ratio of 0.3:1 to 3:1 and a buffer, wherein the buffer is at least one of an amino acid, betaine, and quat, and a molar ratio of buffer to aluminum is at least 0.1:1, at a temperature of 50° C. to 100° C. for a period of time of 1 hour to 6 hours to obtain a first aluminum salt solution;
   II) adding to the first aluminum salt solution an aqueous solution of an inorganic base to obtain a second pH adjusted aluminum salt solution having an OH:Al molar ratio of at most 2.6:1;
   III) heating the second pH adjusted aluminum salt: solution at a temperature of 50° C. to 100° C. for a period of time of at least 6 hours to obtain a third aluminum salt solution containing an $Al_{30}$ polyhydroxyoxoaluminum cation;

IV) heating the third aluminum salt solution to form a fourth aluminum salt at one of
   a) at a temperature of 100° C. to 250° C. in an isochoric reactor or under hydrothermal reaction for a time sufficient to form a species of polyhydroxyoxoaluminum cation detectable at 76 ppm by $^{27}$Al NMR; or
   b) at 100° C. at reflux for about 10 days or greater; and
V) optionally adding an aqueous solution containing a zirconium compound to the second pH adjusted aluminum salt solution to thereby obtain a second pH adjusted aluminum-zirconium salt solution having a molar ratio of aluminum to zirconium of 5:1 to 10:1.

3. The method of claim 1, wherein the inorganic salt is at least one chloride salt chosen from calcium chloride, strontium chloride, barium chloride, and yttrium chloride.

4. The method of claim 1, wherein the buffer is glycine.

5. The method of claim 2, wherein the buffer is glycine.

6. The method of claim 1, wherein the inorganic salt is calcium chloride and the buffer is glycine.

7. The method of claim 1, wherein heating in the isochoric reactor or under hydrothermal reaction is one of
   i) at 100° C. for about 5 days,
   ii) at 120° C. for about 12 hours, or
   iii) at 150° C. for about 20 minutes.

8. The method of claim 2, wherein heating in the isochoric reactor or under hydrothermal reaction is one of
   i) at 100° C. for about 5 days,
   ii) at 120° C. for about 12 hours, or
   iii) at 150° C. for about 20 minutes.

9. The method of claim 1, wherein the fourth aluminum salt exhibits a SEC chromatogram having a SEC Peak 4 area of at least 90% of a total area of Peaks 1, 2, 3, 4 and 5 in the SEC chromatogram.

10. The method of claim 2, wherein the fourth aluminum salt exhibits a SEC chromatogram having a SEC Peak 4 area of at least 90% of a total area of Peaks 1, 2, 3, 4 and 5 in the SEC chromatogram.

11. The method of claim 2, wherein the inorganic base includes at least one member chosen from calcium hydroxide, strontium hydroxide, barium hydroxide, calcium oxide, strontium oxide, barium oxide, calcium carbonate, barium carbonate, strontium carbonate, yttrium hydroxide, yttrium oxide, and yttrium carbonate.

12. The method of claim 11, wherein the inorganic, base is calcium hydroxide.

13. The method of claim 2, wherein the second pH adjusted aluminum salt solution has an OH to Al molar ratio of 2:1 to 2.5:1.

14. The method of claim 2, wherein the first aluminum salt is an aluminum chloride compound chosen from aluminum trichloride, aluminum chlorohexahydrate, and aluminum dichlorohydrate.

15. The method of claim 2, wherein the composition further comprises zirconium and step V) is present in the method.

16. The method of claim 15, wherein the zirconium compound is at least one of $ZrOCl_2.8H_2O$ and Oxo-Hexameric Zirconium-Octaamino Acid.

17. The method of claim 1, wherein the $^{27}$Al NMR spectrum has a species distribution including at most 5% $Al_{13}$ polyhydroxyoxoaluminum cation in the species detectable by $^{27}$Al NMR within the fourth aluminum salt.

18. The method of claim 2, wherein the $^{27}$Al NMR spectrum has a species distribution including at most 5% $Al_{13}$ polyhydroxyoxoaluminum cation in the species detectable by $^{27}$Al NMR within the fourth aluminum salt.

19. The method of claim 1, wherein the fourth aluminum salt has a SEC Peak 4 area of at least 95% of a total area of Peaks 1, 2, 3, 4 and 5 in the SEC chromatogram.

20. The method of claim 2, wherein the fourth aluminum salt has a SEC Peak 4 area of at least 95% of a total area of Peaks 1, 2, 3, 4 and 5 in the SEC chromatogram.

21. The method of claim 1, wherein the fourth aluminum salt has a SEC Peak 3 area of less than 5% of a total area of Peaks 1, 2, 3, 4 and 5 in the SEC chromatogram.

22. The method of claim 2, wherein the fourth aluminum salt has a SEC Peak 3 area of less than 5% of a total area of Peaks 1, 2, 3, 4 and 5 in the SEC chromatogram.

23. The method of claim 2, wherein the third aluminum salt has a SEC Peak 5 area of less than 5% of a total area of Peaks 1, 2, 3, 4 and 5 in the SEC chromatogram.

24. The method according to claim 2, wherein in step III) the period of time is at least 12 hours.

* * * * *